United States Patent
Manhes et al.

(10) Patent No.: US 6,663,751 B2
(45) Date of Patent: Dec. 16, 2003

(54) DEVICE FOR EVAPORATION AND CONDENSATION IN CONFINED ENVIRONMENT

(75) Inventors: Gérard Manhes, Sevres (FR); Christa Gopel, Paris (FR)

(73) Assignee: Analab (SARL), Hoerdt (FR)

( * ) Notice: Subject to any disclaimer, the term of this patent is extended or adjusted under 35 U.S.C. 154(b) by 0 days.

(21) Appl. No.: 10/110,746

(22) PCT Filed: Jul. 16, 2001

(86) PCT No.: PCT/FR01/02308
§ 371 (c)(1),
(2), (4) Date: Apr. 16, 2002

(87) PCT Pub. No.: WO02/05961
PCT Pub. Date: Jan. 24, 2002

(65) Prior Publication Data
US 2002/0148717 A1 Oct. 17, 2002

Related U.S. Application Data

(60) Provisional application No. 60/256,919, filed on Dec. 21, 2000.

(30) Foreign Application Priority Data

Jul. 17, 2000 (FR) .............................................. 00 09322

(51) Int. Cl.⁷ .............................. B01D 3/02; B01L 3/16
(52) U.S. Cl. ..................... 202/237; 202/267.1; 202/269; 422/101
(58) Field of Search ........................... 159/44, DIG. 15, 159/DIG. 41, DIG. 42; 203/1, 100, 2, 99, 86; 202/237, 83, 267.1, 269, 160, 181; 422/99–102

(56) References Cited

U.S. PATENT DOCUMENTS

| | | | |
|---|---|---|---|
| 3,763,014 A | * 10/1973 | Barba et al. | 202/173 |
| 4,617,093 A | 10/1986 | Hwang | |
| 4,846,935 A | 7/1989 | Giesselmann et al. | |
| 4,980,098 A | * 12/1990 | Connery | 261/112.1 |
| 5,142,873 A | 9/1992 | Ramsey | |
| 6,338,774 B1 | * 1/2002 | Lehman | 202/83 |

* cited by examiner

*Primary Examiner*—Virginia Manoharan
(74) *Attorney, Agent, or Firm*—Young & Thompson

(57) ABSTRACT

The device for evaporation and condensation in a closed environment includes an evaporation receptacle, a heating unit for the evaporation receptacle and a condensation receptacle connected in a substantially sealed manner to the evaporation receptacle. The evaporation and condensation receptacles are connected to each other, at their openings, extending on either side of a common separation plane in such a way that the arrangement of the receptacles forms substantially an inverted "V" with a sharp point and in that substantially the entire surface area of the wall forming the evaporation receptacle is brought, by the heating unit, to the same temperature $T_1$ higher than the highest temperature $T_2$ of the wall forming the condensation receptacle.

15 Claims, 3 Drawing Sheets

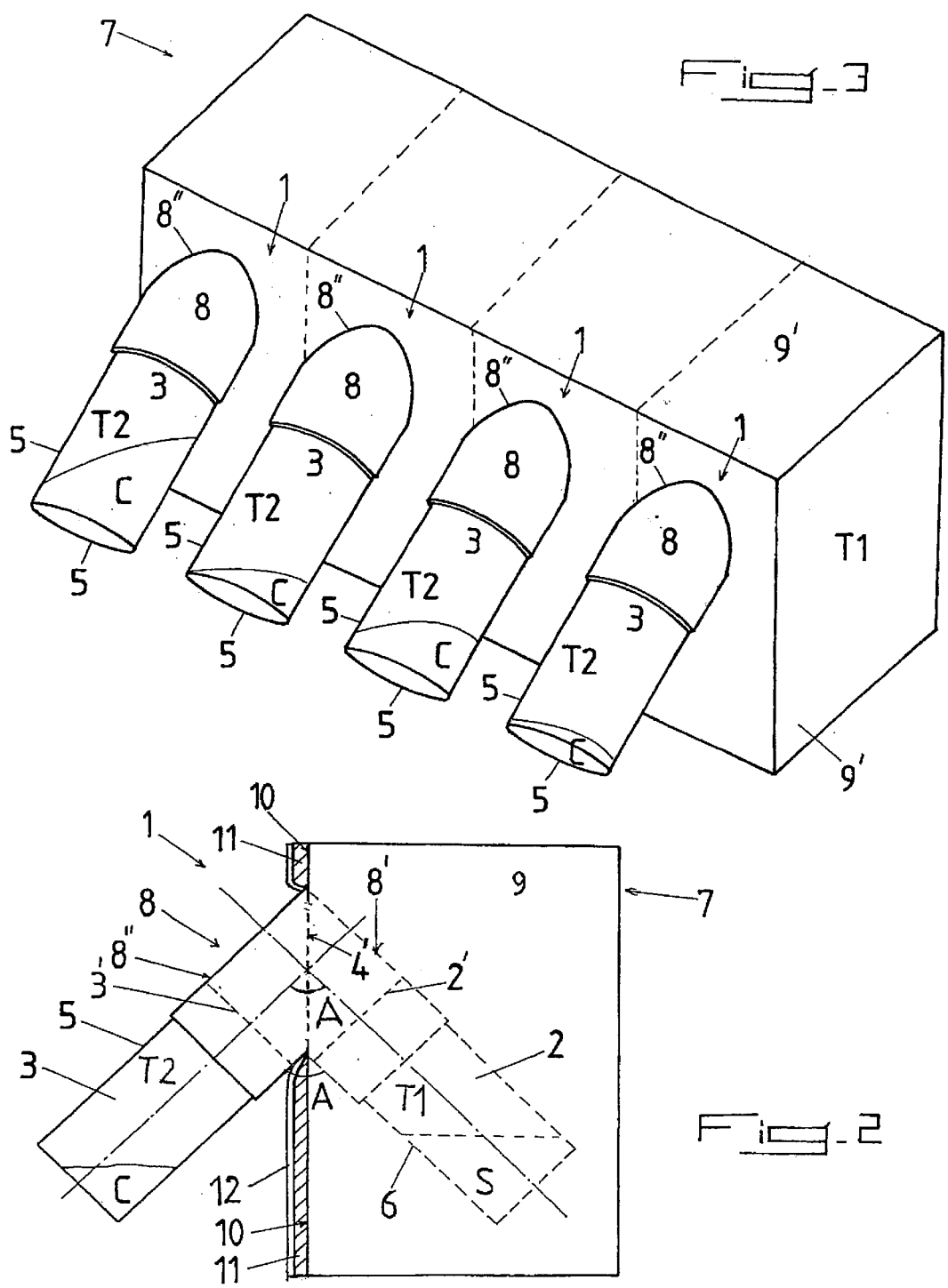

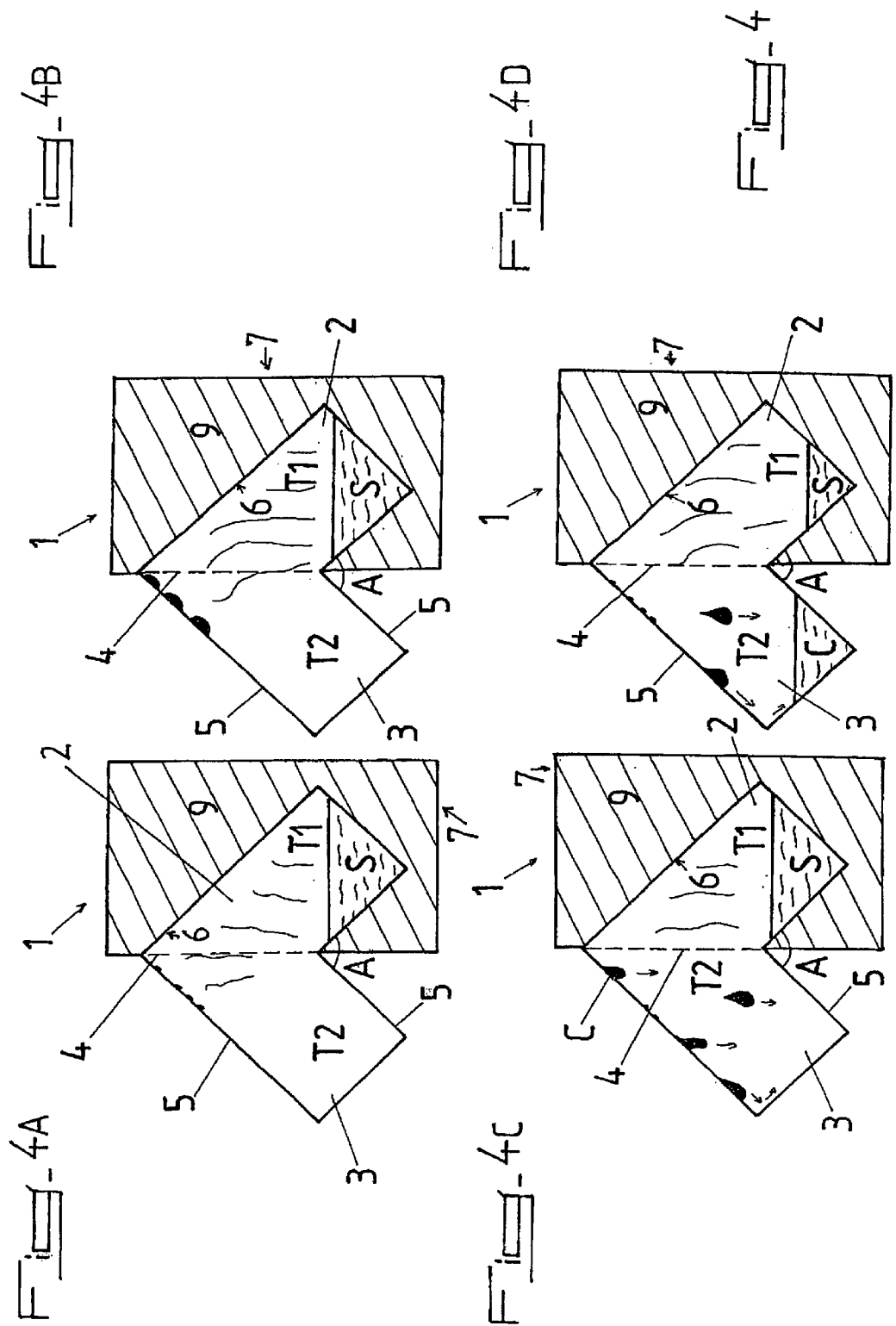

DEVICE FOR EVAPORATION AND CONDENSATION IN CONFINED ENVIRONMENT

This application claims the benefit of U.S. Provisional Application No. 60/256,919, filed Dec. 21, 2000.

FIELD OF THE INVENTION

The present invention relates to the field of laboratory apparatus, especially that for preparing samples for chemical analysis and in particular to evaporator-condenser apparatus. Its object is a device for evaporation and condensation in a closed environment.

BACKGROUND OF THE INVENTION

During qualitative and/or quantitative chemical characterisation, particularly of solid bodies, it is almost always necessary to prepare samples before carrying out the analysis proper which enables their composition to be determined.

A conventional preparation process in chemistry is known by the name "wet process" and involves dissolving the organic or mineral substances to be examined using suitable solvents or reagents in order to "released" the compounds which can be collected and measured in the physicochemical or isotopic measuring apparatus normally used (HPLC, NMR, IR spectrophotometry, atomic absorption, etc.).

For solid inorganic compounds, particularly concentrated and corrosive mineral reagents are generally used, such as strong acids or mixtures of strong acids, strong bases or mixtures of strong bases which, in addition, sometimes have to be heated.

As to the solvents normally used to dissolve organic compounds, these are often harmful, even toxic, to man and his environment.

The end result of dissolving the sample (and any subsequent chemical stages such as neutralisation, filtration, precipitation, solvent substitution, etc.) is therefore a liquid solution of a more or less large volume which has to be reduced in order to concentrate the "released" substances to be analysed. In some cases, it may even be necessary to remove completely the liquid or liquids used to prepare the sample to obtain what is known as a dry residue.

This concentration operation is conventionally carried out by heating said solution in a suitable receptacle and by evaporating the liquids or solvents under an extraction hood and/or by using evaporators. Known evaporators are, for example, evaporators supplied by a specific gaseous stream or rotating evaporators that allow at least a proportion of the evaporated solvents and reagents to be recovered and recycled.

However, evaporation in so-called "open" environments poses many problems with regard to safety and environmental protection. In deed, the vapours of the chemical solvents or reagents contained in the solutions to be concentrated are generally harmful to the health of the operator, to the equipment (pipes, filters, etc.), and even dangerous (risk of fire or explosion), In addition, ever stricter environmental standards entail putting in place complex devices to neutralise and filter the solvent-charged air sucked in by the hoods and/or the charged gases leaving gaseous stream evaporators before their discharge to the atmosphere.

In addition, the air or gases reaching the hood or gaseous stream evaporators risk contaminating the sample to be analysed, which may lead to subsequent erroneous measurements, particularly where detection of the presence of trace elements is concerned. In certain cases it may therefore be necessary to ensure that the entering air or gases are suited to the type of solution to be treated and/or are particularly pure, which is neither practical nor economic.

Although evaporators supplied by a specific gas stream prevent the dissemination of evaporated reagents in the extraction hood, using them is still a constraint in that it involves handling samples in sequence.

Rotating evaporators also have a number of drawbacks. They are relatively sophisticated, small in size, difficult to maintain, fragile when handled and, because of their complexity, relatively expensive. In addition, they are not suited to the evaporation of certain particularly corrosive inorganic reagents such as hydrofluoric acid, for example.

SUMMARY OF THE INVENTION

The object of the present invention in particular is to overcome these disadvantages.

To this end, it concerns a device for evaporation and condensation in a closed environment comprising essentially an evaporation receptacle, a heating means for said evaporation receptacle and a condensation receptacle connected in a substantially sealed manner to said evaporation receptacle, characterised in that said evaporation and condensation receptacles are connected to each other, at their openings, extending on either side of a common separation plane, in such a way that the arrangement of said receptacles forms substantially an inverted "V" with a sharp point and in that substantially the entire surface of the wall forming the evaporation receptacle is brought, by said heating means, to the same temperature $T_1$ higher than the highest temperature $T_2$ of the wall forming the condensation receptacle.

BRIEF DESCRIPTION OF THE DEVICE

The invention will be better understood through the description below which relates to preferred embodiments, given as non-limiting examples, and shown in the accompanying drawings, in which:

FIG. 2 illustrates, diagrammatically, a cross section of a second embodiment of the device according to the present invention;

FIG. 3 illustrates, diagrammatically, a view in perspective of the device according to FIG. 2, and, FIGS. 4a to 4d are simplified diagrams of the operation of the device according to the present invention;

DETAILED DESCRIPTION OF THE INVENTION

Figure 1:
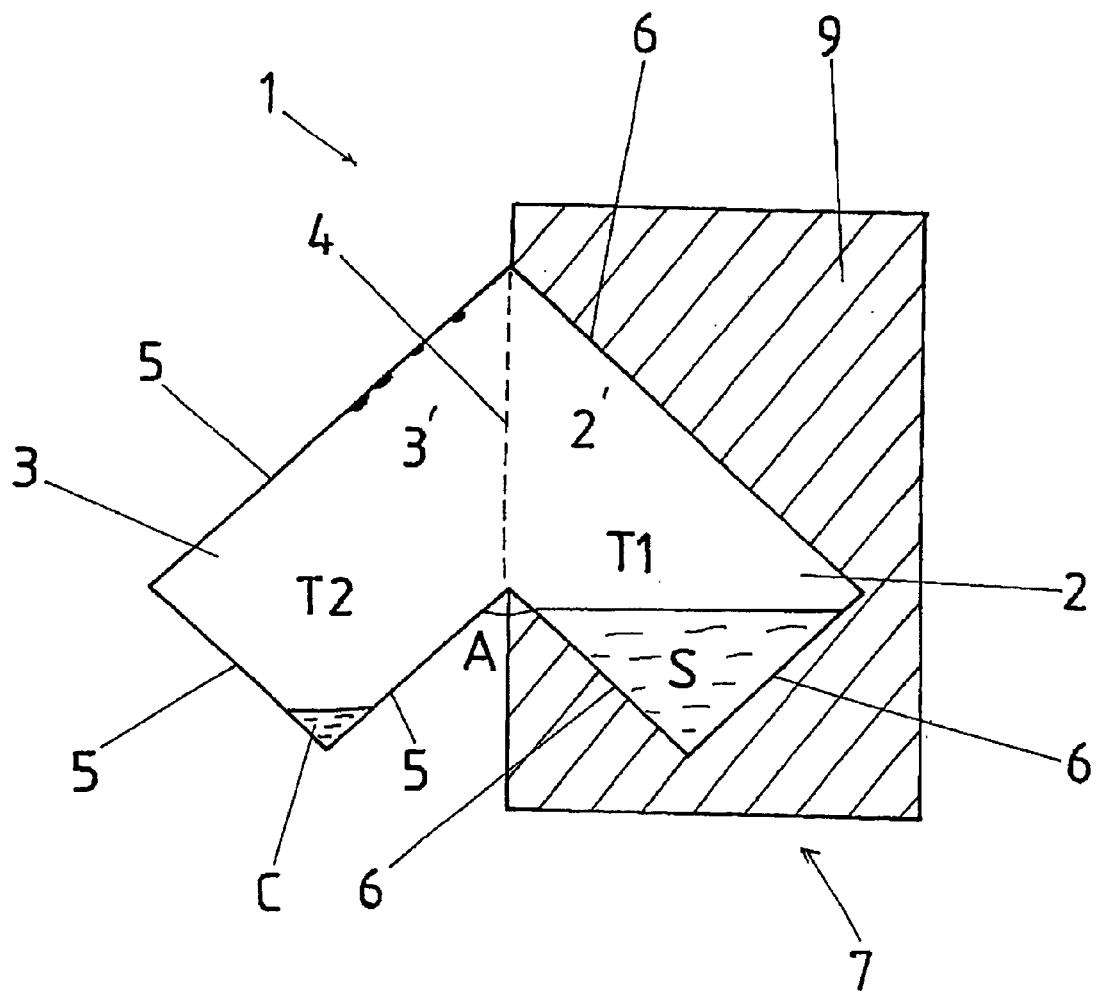
FIG. 1 illustrates, diagrammatically, a cross section of a first embodiment of the device according to the present invention.

In accordance with the invention, and as shown in FIG. 1, the device for evaporation and condensation in a closed environment essentially consists of an evaporation receptacle 2, a heating means 7 for said evaporation receptacle 2 and a condensation receptacle 3 connected in a substantially sealed manner to said evaporation receptacle 2.

According to a first embodiment illustrated in cross section in FIG. 1, the device 1 according to the present invention is characterised in that said evaporation 2 and condensation 3 receptacles are connected to each other, at their openings 2', 3', extending on either side of a common separation plane 4 in such a way that the arrangement of said receptacles 2, 3 forms substantially an inverted "V" with a sharp point and in that substantially the entire surface of the wall 6 forming the evaporation receptacle 2 is brought, by said heating means 7, to the same temperature $T_1$ higher than the highest temperature $T_2$ of the wall 5 forming the condensation receptacle 3.

The materials forming the evaporation receptacle 2 and the condensation receptacle 3 and/or the production of the connection between said receptacles 2, 3 are chosen so as to resist the reagents and solvents used to treat the sample to be analysed.

The solution S to be concentrated is poured into the evaporation receptacle 2 while the condensation receptacle 3 is provided to collect the condensate C which accumulates there as the solution S is evaporated. The device 1 therefore allows the reagents or solvents to be condensed just after they have evaporated.

Completely isolated from the outside environment, the device 1 according to the invention does not require sweeping by a gaseous stream over the solution S to be concentrated in order to evacuate the vapour emitted during the evaporation of said solution S containing the substances to be analysed.

It therefore allows all the normal evaporation and condensation operations to be carried out economically and in complete safety. The device 1 according to the invention allows in particular the emission, into the ambient air of the laboratory and then into the atmosphere, of substances harmful to the health of the operator, to the industrial equipment and to the environment, to be avoided.

Condensation of the evaporated solubilising reagents in the form of condensates C in the condensation receptacle 3 allows those condensates to be recovered in a concentrated form for storage or treatment before disposal or recycling.

The device 1 according to the invention makes it possible to work, if necessary, under extraction hoods operating with low air throughput and requires no or few measures to treat the air stream evacuated by said hoods. It therefore permits economy in the construction of laboratories and in their operating cost. It also allows a reduction in the energy consumption of the existing hoods which no longer need to operate constantly at full speed during such handling.

In addition, the device 1 according to the invention eliminates possible contamination of the samples by the air or gaseous stream sweeping the surface of said samples during evaporation.

The device 1 is also simpler to use than the existing evaporators and more flexible in that it allows the samples to be concentrated to be treated individually.

In a second embodiment illustrated in FIG. 2, the device 1 according to the present invention is characterised in that the evaporation 2 and condensation 3 receptacles are connected at their openings 2', 3', by means of an elbow piece 8 with straight edges containing the common separation plane 4'.

Unlike the first embodiment described above in which the evaporation 2 and condensation 3 receptacles were connected directly to each other, for example by screwing, bonding, welding or similar, the evaporation 2 and condensation 3 receptacles are here connected by means of an elbow piece 8.

This measure allows in particular for easier assembly and dismantling of the device 1 for example to supply, empty, change, repair or clean the above-mentioned evaporation 2 and condensation 3 receptacles.

According to a further advantageous characteristic, the sectional area of the evaporation receptacle 2 situated in the vicinity of the common separation plane 4, 4' is smaller than or equal to the area of said common separation plane 4, 4'. This optimisation of the area of the common separation plane 4, 4' allows an increase in speed of execution of the concentration operation and therefore an increase in the economic viability of the device 1.

As previously mentioned, a particularly preferred embodiment of the present invention is characterised in that the evaporation 2 and condensation 3 receptacles are fixed removably on the elbow piece 8, for example by providing screw threads on the walls 6, 5 of said receptacles 2, 3 and of said elbow piece 8. Of course, all the other usual temporary fixing methods may also be envisaged (connection by catching, by hooks, fasteners, nuts, etc.) and the various fixings may be equipped, if necessary, with suitable sealing means, such as joints, membranes or similar.

According to a further characteristic of the present invention, the device 1 is characterised in that the evaporation 2 and condensation 3 receptacles are identical. Advantageously, this allows the evaporation 2 and condensation 3 receptacles to be transposed if necessary or if desired. This characteristic also allows a reduction in the quantity of evaporation 2 and condensation 3 receptacles stored in reserve.

In a particularly advantageous way the device according to the invention is characterised in that the angle A between the arms of the inverted ",V" formed by the longitudinal axes of the evaporation 2 and condensation .3 receptacles is between 30° and 150°, and preferably equal to about 90°, which for a reasonable size results in adequate flow rates of the condensates C along the walls 5 of the condensation receptacle 3.

According to a further characteristic, the evaporation receptacle 2 and/or condensation receptacle 3 are produced in the form of cylindrical tubes.

Thus standard laboratory equipment or equipment sufficiently close to standard laboratory equipment can be used to handle the solution S or the condensate C before or after using the device 1 according to the present invention.

As explained earlier, the cylindrical tube or tubes may be provided with a means of screwing said tube or tubes into the elbow piece 8.

As illustrated by way of non-limiting examples in FIGS. 1 to 3, the device 1 is again advantageously characterised in that the evaporation receptacle 2 is entirely contained in a thermal enclosure 9, 9' of adjustable temperature, the common separation plane 4, 4' of the evaporation 2 and condensation 3 receptacles being situated at and in the plane of one of the walls 10 of said thermal enclosure 9, 9'.

Thus, the common separation plane 4, 4' which is common to the evaporation 2 and condensation 3 receptacles and which delimits the surface from which the evaporated liquid can condense, may, as can clearly be seen in FIGS. 1 to 3, be situated in the vertical plane of one of the vertical walls of the thermal enclosure 9, 9', the coldest part (condensation receptacle 3 and unheated portion 8" of the elbow piece 8) being situated outside said thermal enclosure 9, 9'.

As illustrated in FIG. 2, a particularly advantageous variant of the device 1 is characterised in that the thermal enclosure 9 is insulated over at least the part of wall 10 situated in the vicinity of the condensation receptacle 3 by means of at least one layer 11 of thermally insulating and/or chemically inert material.

If said at least one layer 11 of insulating material is not sufficiently resistant to chemical attack, it can in turn advantageously be covered by an additional protective layer 12 of said layer 11 made of a more chemically suitable material, for example a PTFE-type fluoropolymer.

In this way, damage to the layer 11 of insulating material during a possible discharge of vapour or corrosive liquid is avoided. In addition, this additional protective layer 12 avoids the risk of burns to the user.

By means of this insulation, the evaporation receptacle 2 (and possibly the heated portion 8') are better maintained at the temperature $T_1$. Similarly, the difference between the temperature T, of the evaporation receptacle 2 and the maximum temperature $T_2$ of the condensation receptacle 3 may better be kept high, which contributes to improving further the performance of the device 1.

The use of the ambient atmosphere as a cooling means for the condensation receptacle 3 is particularly advantageous, both economically and because of its convenience and safety of use compared with a possible additional cooling device. The addition of a supplementary cooling means, for example a cooler using water or chemical coolant is however still possible, particularly if a further improvement in the performance of said device 1 is required.

With regard to the material constituting the evaporation receptacle 2, and the heated portion 8' of the elbow piece 8, a material resistant to the corrosive chemical substances used when solubilising the samples to be analysed ($H_2SO_4$, $HNO_3$, HF, HCl, $H_3PO_4$, NaOH, KOH, etc.), will be chosen and preferably a material with high thermal conductivity.

The condensation receptacle 3 and the unheated portion 8" of the elbow piece 8 will advantageously be made of a material that is also resistant to the above-mentioned corrosive substances.

Suitable materials for producing the unheated portion 8" of the elbow piece 8 are, for example, quartz, fluoropolymers, etc.

Of course, the elbow piece 8 may also be made of a single piece in a single chemically resistant and inert material, for example a PTFE-type fluoropolymer.

FIG. 3 is a perspective view of an evaporator and condenser device comprising a plurality of devices 1 (whose visible sections only are illustrated for greater clarity) according to the present invention. The four devices 1 are arranged in the form of modules in a single thermal enclosure 9'. The interior of such a single thermal enclosure 9' may for example be provided or produced from a solid block of a material that conducts heat well, run through by electrical resistances, and completely enveloping all or substantially all the walls 6 of the evaporation receptacle 2 (possibly the heated portions 8' of the elbow piece 8) in order to obtain a homogeneous temperature $T_1$ over said walls 6 and sections 8' and inside said evaporation receptacle 2. Graphite, for example, is particularly suitable for producing a solid heating block for a single thermal enclosure 9'.

As can be seen in FIGS. 4a to 4d, the device 1 according to the present invention functions in outline in the manner set out below.

The solution to be evaporated S is introduced into the evaporation receptacle 2 of the device 1 by some supply means (not illustrated) such as a reclosable opening, a connection to an external reservoir, etc.

If the evaporation receptacle 2 is removable, the liquid to be evaporated can simply be poured manually into said receptacle before being put or replaced onto the device 1, in particular fixed on the elbow piece 8. Removable evaporation 2 and condensation 3 receptacles are particularly useful if the nature of the solution to be evaporated may often change or if cleaning is necessary. Removable receptacles 2, 3 also allow easier and faster replacement, for example in case of damage to one of said receptacles or to adapt the volume or physico-chemical properties of said receptacles to the quantity or nature of the solution S to be evaporated.

When the solution S is in place in the evaporation receptacle 2, the elbow piece 8 provided with the condensation receptacle 3 may be fixed to said evaporation receptacle 2, for example by screwing or clipping ensuring that there is a good seal between the various connected elements.

The external wall 6 of the evaporation receptacle 2 and if applicable the wall of the heated portion 8' of the elbow piece 8, are then placed in contact over all or substantially all their surface area with the heating means 7.

In the non-limiting embodiments illustrated in FIGS. 1 to 4, the evaporation receptacle 2 is introduced into a thermal enclosure 9, 9' whose internal shape perfectly matches said evaporation recipient 2, thus ensuring close thermal contact. As can be seen very clearly in FIG. 2, the condensation receptacle 3 and the wall of the unheated portion 8" of the elbow piece 8 are not heated by the heating means 7 and are therefore at lower temperatures than $T_1$ prevailing in said evaporation receptacle 2 when said heating means 7 is put into operation.

It should be noted that unlike the evaporation receptacle 2, the condensation receptacle 3 is not at a single temperature but that there is a thermal gradient inside said condensation receptacle 3, whose maximum temperature $T_2$ is lower than $T_1$ so that condensation can take place.

The temperature $T_1$ is set and regulated by the heating means 7 in such a way that the constituents to be extracted from the solution S evaporate, without however causing harmful boiling within said solution S. A suitable range of temperatures may, for example, be between 40° C. and 300° C. according to the solutions S to be treated.

As can be seen in FIGS. 4a to 4d, moderate heating (simmering) of the solution S causes droplets of condensates C to appear on the colder walls of the condensation receptacle 3. As illustrated, these droplets form only on the left side in the region of the point of the upper inverted "V" and slide along the wall of the condensation receptacle 3 (more or less rapidly according to the inclination due to the angle A and the internal composition of the wall 5 of the condensation receptacle 3) to accumulate in the form of a condensate C at the bottom of the condensation receptacle 3.

As shown in FIGS. 4c and 4d, the particular geometry in the shape of an inverted "V" with an acute angle of the device 1 prevents the droplets of condensate C formed at the point of the upper inverted "V" from falling back under their own weight into the solution S to be evaporated. In fact, the above-mentioned acute angle allows the condensed droplets to be collected at the bottom of the condensation receptacle 3 and the uncondensed vapours of the evaporation receptacle 2 to be separated and kept on either side of the common separation plane 4, 4'. Consequently, the point of the upper inverted "V" forms a sort of upper groove acting as linear one-dimensional frontier on which no droplet (three-dimensional) can form.

Similarly, the acute angle of the lower inverted "V", close to the bottom of evaporation 2 and condensation 3 receptacles, forms a sharp lower ridge acting as a second one-dimensional frontier for the condensed droplets that are formed on the left section of the upper groove formed by the upper inverted "V", since the droplets can only fall on the left side of the common separation plane 4, 4', in other words in the bottom of the condensation receptacle 3. The evaporation process is therefore greatly accelerated.

Finally, the device 1 according to the present invention also allows much greater flexibility in that evaporation can be conducted on large volumes of solution S.

The device 1 of the present invention therefore provides a simple and efficient evaporator-condenser that is easy and safe to use and maintain.

It goes without saying that the device 1 according to the present invention is preferably made of materials that meet the above-mentioned requirements as to chemical resistance to attack caused by chemical reagents or solvents that may subsist in the solution S to be evaporated and, preferably, the usual requirements as to thermal conduction.

Such materials may be selected from a varied range such as, by way of example, various types of glass, plastic materials (in particular fluoropolymers such as PTFE), metals or special alloys, etc.

According to another particularly useful characteristic, the material used to manufacture the evaporation 2 and/or condensation 3 receptacle or receptacles is a transparent or translucent material allowing a visual check of the levels in said receptacles 2, 3.

Of course, the invention is not restricted to the embodiments described and illustrated in the accompanying drawings. Modifications remain possible, particularly from the point of view of the composition of the various elements or by substitution of technical equivalents, without however departing from the scope of protection of the invention.

What is claimed is:

1. A device for evaporation and condensation in a closed environment comprising:

an evaporation receptacle;

a heating means for said evaporation receptacle; and a condensation receptacle connected in a substantially sealed manner to said evaporation receptacle, wherein said evaporation and condensation receptacles are connected to each other, at their openings, extending on either side of a common separation plane in such a way that an arrangement of said receptacles forms substantially an inverted "V" with a sharp point and said heating means heating a substantially entire surface of wall forming the evaporation receptacle to a temperature higher than a highest temperature of a wall forming the condensation receptacle.

2. The device according to claim 1, wherein the evaporation and condensation receptacles are connected at their openings, by means of an elbow piece with straight edges containing the common separation plane.

3. The device according to claim 2, wherein the evaporation and condensation receptacles are fixed removably on the elbow piece.

4. The device according to claim 3, wherein the evaporation and condensation receptacles are identical.

5. The device according to claim 2, wherein a surface area of the evaporation receptacle situated in the vicinity of the common separation plane is smaller than or equal to the surface area of said common separation plane.

6. The device according to claim 5, wherein the evaporation and condensation receptacles are fixed removably on the elbow piece.

7. The device according to claim 1, wherein a surface area of the evaporation receptacle situated in the vicinity of the common separation plane is smaller than or equal to a surface area of said common separation plane.

8. The device according to claim 7, wherein the evaporation and condensation receptacles are fixed removably on the elbow piece.

9. The device according to claim 1, wherein an angle between arms of the inverted "V" formed by longitudinal axes of the evaporation and condensation receptacles is between 30° and 150°.

10. The device according to claim 9, wherein the angle is about 90°.

11. The device according to claim 1, wherein at least one of the evaporation receptacle and the condensation receptacle is produced as a cylindrical tube.

12. The device according to claim 11, wherein the cylindrical tube comprises a means for screwing said tube into the elbow piece.

13. The device according to claim 1, further comprising a thermal enclosure of adjustable temperature entirely containing the evaporation receptacle and the common separation plane of the evaporation and condensation receptacles situated at and in the plane of one wall of said thermal enclosure.

14. The device according to claim 13, further comprising at least one layer of at least one of thermally insulating material and chemically inert material insulating the thermal enclosure over at least part of a wall situated in the vicinity of the condensation receptacle.

15. The device according to claim 1, wherein at least one of the evaporation and condensation receptacles is made of a transparent or translucent material allowing a visual check of said receptacle.

* * * * *